United States Patent [19]

Zaltsman

[11] Patent Number: 4,526,472
[45] Date of Patent: Jul. 2, 1985

[54] MIXING CAPSULE ASSEMBLY
[75] Inventor: Saul Zaltsman, Savyon, Israel
[73] Assignee: Silmet Ltd., Givatayim, Israel
[21] Appl. No.: 641,255
[22] Filed: Aug. 16, 1984
[30] Foreign Application Priority Data Oct. 21, 1983 [IL] Israel ............................. 70025

[51] Int. Cl.$^3$ ............................. B65D 25/08
[52] U.S. Cl. ..................... 366/108; 206/219; 366/602
[58] Field of Search .............. 366/108, 602; 206/63.5, 206/219–222, 568, 216; 241/199, 199.6, 199.9, 291; 215/6, DIG. 8

[56] References Cited

U.S. PATENT DOCUMENTS

| 4,182,447 | 1/1980 | Kay .................................. 366/602 X |
| 4,362,242 | 12/1982 | Cheetham ......................... 366/602 X |
| 4,433,779 | 2/1984 | Schmid, Jr. et al. ............. 366/602 X |
| 4,450,958 | 5/1984 | Prasad ............................. 366/602 X |

Primary Examiner—Timothy F. Simone
Attorney, Agent, or Firm—Benjamin J. Barish

[57] ABSTRACT

A mixing capsule assembly, particularly for use in preparing dental amalgams, comprises an outer capsule for receiving one of the materials to be mixed, and an inner capsule to receive a second material to be mixed and to be enclosed within the outer capsule. The inner capsule includes two sections attachable together by complementary frictionally-engaging surfaces of conical configuration. The arrangement is such that when the inner capsule is impacted against an inner face of the outer capsule during the vibration of the assembly, the complementary surfaces are moved away from each other to permit some of the second material to pass between them and to mix with the material in the outer capsule; and when the inner capsule is impacted against the opposite inner face of the outer capsule, the complementary surfaces are moved back to block the passage of material between them.

13 Claims, 4 Drawing Figures 4,526,472

MIXING CAPSULE ASSEMBLY

BACKGROUND OF THE INVENTION

The present invention relates to capsule assemblies for mixing two or more materials, and particularly of the self-actuating type of capsule assemblies in which the materials to be mixed are normally separated but are brought together automatically upon vibrating the assembly. Such mixing capsule assemblies are commonly used in preparing dental amalgams. The invention is therefore described below with respect to this application, but it will be appreciated that the invention could advantageously be used in many other situations as well.

Many diverse types of mixing capsules have been designed particularly for use in producing dental amalgams by mixing mercury with a powder. Among the known types of mixing capsules are those which include two compartments separated by a friction-fitted barrier which is removed upon mixing, or by a web which is ruptured upon mixing. Another known type includes an outer capsule containing one material, and an inner capsule containing the other, e.g. mercury, which inner capsule is in the form of a sealed aluminum foil or plastic bag which is ruptured upon mixing. In another known type, the inner capsule is in the form of a container having a fine outlet opening and a ball frictionally received within the container so as to cover and uncover the opening during the vibration of the capsule. The foregoing known types of mixing capsules, however, are not entirely satisfactory from all the standpoints of assuring complete separation of the two materials until mixing is to be effected, and promoting the thorough mixing of the two materials when the capsule is vibrated, while still retaining a simple inexpensive construction susceptible to volume production at low cost.

An object of the present invention is to provide a novel mixing capsule assembly having advantages in the above respects.

SUMMARY OF THE INVENTION

According to a broad aspect of the present invention, there is provided a mixing capsule assembly for mixing a plurality of materials by vibration, comprising: an outer capsule to receive one of the materials to be mixed; and an inner capsule to receive a second material to be mixed and to be enclosed within the outer capsule; the inner capsule including two sections attachable together to enclose the second material and to prevent it from mixing with the first material; the two sections of the inner capsule being attachable together by at least one pair of complementary, frictionally-engaging surfaces configured such that when the inner capsule is impacted against one inner face of the outer capsule during the vibration of the capsule assembly, the complementary surfaces are moved away from each other to permit some of the second material to pass therebetween and to mix with the one material, and when the inner capsule is impacted against the opposite inner face of the outer capsule during the vibration of the capsule assembly, the complementary surfaces are moved back against each other to block the passage therebetween of the second material.

More particularly, the pair of complementary surfaces are constituted by the sides of a bore formed in one of the sections, and the sides of a stem formed in one end of the other of the sections. In addition, in both of the described embodiments, the opposite ends of the two sections are also in frictional engagement with each other.

In one described embodiment, the bore in one section is of conical configuration, increasing in diameter from the outer to the inner end thereof, and the outer end of the stem in the other section is of complementary conical configuration and normally projects past the outer face of the one section so as to be impacted against the inner face of the outer capsule during the vibration of the capsule assembly.

In a second described embodiment, the bore in one section decreases in diameter from the outer end to the inner end thereof, and the outer end of the stem in the other secti section is of complementary conical configuration and normally is recessed within the bore so that the one section of the inner capsule is impacted against the inner face of the outer capsule during the vibration of the capsule assembly, causing the stem to move further within the bore and thereby to permit the passage of the second material therethrough. In the latter described embodiment, the opposite end of the one section projects past the respective outer face of the other section such as to be impacted by the inner face of the outer capsule during the vibration of the capsule assembly, and thereby to permit some of the second material therein also to pass between the complementary surfaces at the opposite ends of the two sections df the inner capsule.

While the invention is particularly useful for mixing two materials, such as in preparing dental amalgams, it will be appreciated that the invention could be used for mixing more than two materials, for example, by including within the outer capsule two or more inner capsules each of which includes a material to be mixed.

Further features and advantages of the invention will be apparent from the description below.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
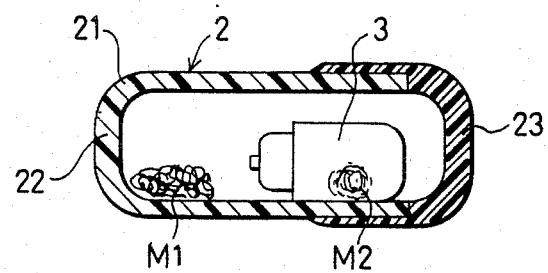
FIG. 1 is a view, partly in section, illustrating one form of mixing capsule assembly constructed in accordance with the present invention.

The mixing capsule illustrated in FIG. 1 comprises an outer capsule, generally designated 2, adapted to receive one of the materials, schematically indicated as M1, to be mixed; and an inner capsule, generally designated 3, adpated to receive the other material, schematically indicated as M2, to be mixed. For purposes of example, the mixing capsule assembly illustrated in FIG. 1 may be for preparing a dental amalgam; in such case, material M2 within the inner capsule 3 is mercury which is to be mixed with a powder material M1 contained within the outer capsule 2, this usually being done by vibrating the capsule assembly in a high-frequency vibrator, e.g. one operating at 3,000 cycles per minute (50 cycles per second) for about five seconds.

The outer capsule 2 is constituted of a main section 21 of cylindrical configuration closed at one end by an end wall 22 and open at the opposite end. A cap 23 is frictionally applied over the open end of section 21 to close it.

The inner capsule 3 is of an overall length slightly less than one-half the length of the other capsule 2. The inner capsule is also constituted of two sections, namely, an inner cylindrical section 31 closed at one end by an end wall 32 formed with a central bore 33, and open at the opposite end; and an outer section 34 also closed at one end by an end wall 35 and open at the opposite end, which latter end is frictionally received over the outer face of the inner section 31. The outer section 34 further includes a stem 36 integrally formed with end wall 35 an and extending axially of section 34. The length of stem 36 is greater than the length of section 34, so that the stem, when section 34 is assembled with section 31, passes through bore 33 of section 31 and projects pa past the outer face of its end wall 32.

Figure 2:
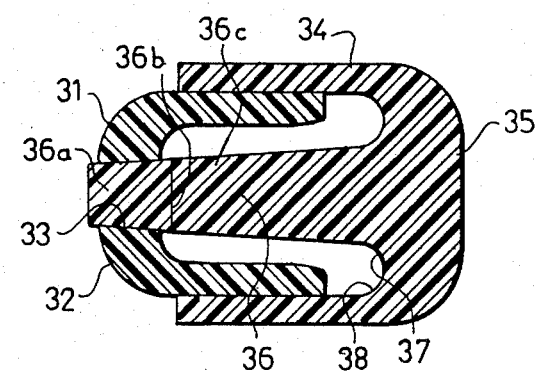
FIG. 2 is an enlarged sectional view illustrating the construction of the inner capsule in the assembly of FIG. 1.

As shown in FIG. 2, bore 33 in end wall 32 is of conical configuration, increasing in diameter from the outer end to the inner end. The outer tip 36a of stem 36 is of complementary conical configuration, also increasing in diameter from the outer end to a line 36b slightly inwardly of the inner face of end wall 32 in the illustrated assembled condition of the inner capsule 3. The remaining portion 36c of stem 36 may also be tapered to provide a curved juncture 37 with end wall 35. The juncture of end wall 35 with the outer cylindrical section 34 is preferably also curved, as shown at 38. Actually, both junctures 37 and 38 may be effected by a semicircular surface between stem 36 and the outer cylindrical wall of section 34.

The capsule assembly illustrated in FIGS. 1 and 2 is used in the following manner:

First, the inner capsule 3 is opened by separating its two sections 31 and 34, and the material M2 (e.g., mercury) is introduced into section 34 whereupon section 31 is attached thereto by press-fitting stem 36 of section 34 through bore 33 of section 31. This causes the opposite end of the inner capsule also to be closed by the engagement of the inner face of section 34 with the outer face of section 31, as shown in FIG. 2.

The outer capsule 2 is then opened by separating its cap 23 from its main section 22. The inner capsule 3 is inserted with the outer capsule 2, and also introduced within capsule 2 is the material M1 (e.g., powder) to be mixed with the material M2 within the inner capsule 3. Cap 23 is then press-fitted over the open end of section 21 to close the outer capsule 2.

The outer capsule 2, with the materials M1 and 122 within it and separated by the walls of the inner capsule 3, may be shipped and stored with the assurance that the material M2 is sealed within the inner capsule 3 and cannot leak out to come into contact with the material M1 within the outer capsule 2.

When the illustrated capsule assembly is to be used, it is merely inserted into the usual vibrator which vibrates the capsule at about 3000 cycles per minute (e.g., 50 cycles per second) parallel to the longitudinal axis of the outer capsule 2. During this operation, the inner capsule 3 is rapidly vibrated within the outer capsule 2, alternatively impacting against end wall 22 of the outer capsule, and against cap 23 at the opposite end of the outer capsule. During the former impacts, the projecting end 36a of stem 36 impacts against the inner face of end wall 22, thereby causing section 31 to move (leftwardly in FIG. 2) with respect to section 34. Thus, relative movement is effected between the conical end 36a of stem 36, and the conical bore 33 in end wall 32, thereby slightly separating the complementary surfaces of these two elements. Material M2 (e.g., mercury) within the inner capsule 3 is set into motion by these vibrations, and same is thus permitted to pass through this space from inside the inner capsule 3 into the outer capsule 2. During the movements of the inner capsule 3 in the opposite direction, i.e., wherein its end wall 35 impacts against the inner face of cap 23, section 31 of the inner capsule will move towards section 34, thereby restoring the seal between the conical end 36a of stem 36 and the conical bore 33 in end wall 32.

It will thus be seen that for each reciprocatory cycle of movement of the inner capsule 3 within the outer capsule 2, the conical end 36a of stem 36 will move sufficiently with respect to conical bore 33 so as to permit some of the material M2 to pass from the interior of the inner capsule 3 into the interior of the outer capsule 2, and to come into direct contact with material M1 in that capsule.

As one example, particularly useful for preparing dental amalgams, the length of the outer capsule 2 was 31 mm.; its inner diameter was 10 mm.; the length of the inner capsule 3, from the outer face of its conical stem 36a to the outer face of end wall 35 was 12 mm., with stem 36a projecting about 0.3–0.5 mm. from the outer face of end wall 32; and the outer diameter of the inner capsule 3, particularly of its outer section 34, was 8.5 mm.

In this example, the outer capsule 2 was made of polypropylene and the inner capsule 3 was made of a harder material, namely, a polycarbonate. Material M2 included within the inner capsule was mercury, and material M1 included externally of the inner capsule but internally of the outer capsule 2 was a powder which, when mixed with mercury, produced a dental amalgam. It was found that after five seconds of vibration in a conventional vibrator operating at 3000 cycles per minute (50 cycles per second), all the mercury M2 left the inner capsule 3 and became thoroughly mixed with the material M1 to produce the desired amalgam.

It will be appreciated that the mixing capsule assembly illustrated in FIGS. 1 and 2 provides a number of important advantages. Thus, after the capsule has been assembled with the two sections 31, 34 of the inner capsule 3 friction-fitted to effect a tight seal with respect to the material M2 within it, a high degree of assurance is provided against leakage of any of the material M2 during the normal handling and storage of the capsule assembly. The illustrated constuction also provides a high degree of assurance that all the material M2 will leave the inner capsule to mix with the material M1 during the normal high-speed vibration of the assembly. Further, the inner capsule 3 while and after dispensing its material M2, serves as a pestle to effect a thorough mixing of the two materials. Moreover, there is no chance of foreign matter entering the mixture, such as the remanents of the barrier or inner bag or foil as in some of the existing mixing capsules. Still further, the capsules can be conveniently filled with the required materials and assembled ready for use. Finally, the parts of the illustrated capsule assembly are few, simple, and susceptible to volume production at low cost.

Figure 3:
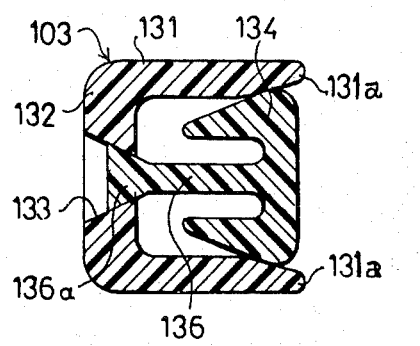
FIG. 3 is a view similar to that of FIG. 2, but illustrating another construction of inner capsule which may be used.

In the above-described FIGS. 1-2 embodiment, it will be seen that the contents of the inner capsule 3 penetrate only through one wall of the capsule during one-half cycles of each complete cycle of vibration. FIG. 3 illustrates a construction of the inner capsule 5 which permits some of its contents to penetrate through the two opposite sides of the capsule, some material during the strokes in one direction, and other material during the strokes in the other direction.

Thus, in the construction of the inner capsule illustrated in FIG. 3, and therein designated 103, there are also two sections 131 and 134 respectively, with section 131 including a conical bore 133 in its end wall 132, and section 134 including a stem 136 having a conical end 136a received within conical bore 133. However, in the construction illustrated in FIG. 3, conical bore 133 is tapered in the opposite direction from that of FIG. 2, namely, decreasing in diameter from the outer face of end wall 132 to its inner space. Conical tip 136a of stem 136 is formed with a complementary surface also decreasing in diameter from its outer face to its inner face. Further, conical tip 136a does not project completely through bore 133, as in FIG. 2, but rather is normally recessed within that bore when in its normal sealing position in that bore, as illustrated in FIG. 3. To facilitate assembling the outer conical portion 136a to the remainder of stem 136, portion 136a may be constructed as a separate element and then assembled to stem 136, as by a press-fit, threads, adhesive, or the like, after section 134 has been press-fitted into section 131 of the inner capsule 103.

In addition, the outer open end 131a of section 131 projects past the outer face of section 134 when the two sections are in their assembled condition, as illustrated in FIG. 3. In addition, the inner face of section 131 at its outer tip 131a is inwardly tapered, as shown at 131b, such that section 134 may be press-fitted into section 131 to provide a seal between face 131b and the outer face of section 134. However, upon movement of section 134 away from bore 133 (i.e., rightwardly in FIG. 3), a space is formed between the inner surface 131b of section 131, and the outer surface of section 134, to permit some of the material within the inner capsule to leave it.

It will thus be seen that when the inner capsule 133 impacts against the end wall 22 of the outer capsule 2 in FIG. 1, the conical portion 136a of stem 136 moves leftwardly within the conical bore 133 to provide a space for permitting some of the material within the inner capsule 103 to leave; and when the open end 131a of the inner capsule 103 impacts against cap 23 of the outer capsule, the inner section 134 moves in the opposite direction, rightwardly in FIG. 3, to close the passage between the conical porition 136a of stem 136 and the bore 133, and to open the passageway between the inner face of section 131 and the outer face of section 134.

Thus, in the construction of inner capsule illustrated in FIG. 3, material (M2) will be ejected out through the capsule during both of the half-cycles of vibration, and therefore will be dispensed at a faster rate than in the capsule illustrated in FIG. 2.

Apart from this, the capsule of FIG. 3 provides all the other advantages as the capsule of FIG. 2, including its function as a pestle during the mixing operation.

Figure 4:
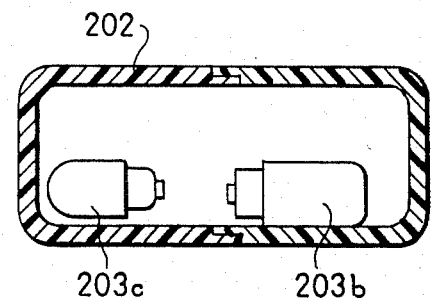
FIG. 4 illustrates a mixing capsule assembly including two inner capsules for mixing three or more materials.

While the invention has been described above with respect to capsule assembles for mixing one material within the outer capsule and a second material within the inner capsule, it will be appreciated that it could be used for mixing more than two materials, for example, by providing two (or more) inner capsules, each according to the construction of FIGS. 2 or 3. This is shown in FIG. 4, wherein a single outer capsule 202 encloses two inner capsules 203a, 203b, each of which capsules may include materials to be mixed, thereby effecting a mixing of three materials.

It will also be appreciated that the materials to be mixed could be included only in the two (or more) inner capsules, and not in the outer capsule, thereby better assuring isolation of the materials until they are to be mixed.

Many other variations, modifications, and applications of the invention will be apparent.

What is claimed is:

1. A mixing capsule assembly for mixing a plurality of materials by vibration, comprising: an outer capsule to receive one of the materials to be mixed; and an inner capsule to receive a second material to be mixed, and to be enclosed within said outer capsule; said inner capsule including two sections attachable together to enclose said second material and to prevent it from mixing with said first material; said two sections of the inner capsule being attachable together by at least one pair of complementary, frictionally-engaging surfaces configured such that when the inner capsule is impacted against one inner face of the of the outer capsule during the vibration of the capsule assembly, said complementary surfaces are moved away from each other to permit some of said second material to pass therebetween and to mix with said one material, and when the inner capsule is impacted against the opposite inner face of the outer capsule during the vibration of the capsule assembly, said complementary surfaces are moved back against each other to block the passage therebetween of said second material; said pair of complementary surfaces being constituted by the sides of a bore formed centrally in one of said sections, and the sides of a stem formed centrally in the other of said sections; the opposite ends of said two sections of the inner capsule being also in frictional engagement with each other.

2. The capsule assembly according to claim 1, wherein said bore in one section is of conical configuration, increasing in diameter from the outer to the inner end thereof, and the outer end of said stem in the other section is of complementary conical configuration and normally projects past the outer face of said one section so as to be impacted against the inner face of the outer capsule during the vibration of the capsule assembly.

3. The capsule assembly according to claim 1, wherein said bore in one section decreases in diameter from the outer end to the inner end thereof, and the outer end of said stem in the other section is of complementary conical configuration and normally is recessed within said bore so that said one section of the inner capsule is impacted against the inner face of the outer capsule during the vibration of the capsule assembly, causing said stem to move further within said bore and thereby to permit the passage of the second material therethrough.

4. The capsule assembly according to claim 3, wherein the opposite end of said one section projects past the respective outer face of the other section such as to be impacted by the inner face of the outer capsule during the vibration of the capsule assembly, and thereby to permit some of said second material therein also to pass between the complementary surfaces at said opposite ends of the two sections of the inner capsule.

5. The capsule assembly according to claim 1, wherein said outer capsule is consituted of two sections having frictionally-engaging surfaces for attaching them together to enclose said one material and the inner capsule.

6. The capsule assembly according to claim 1, wherein said outer capsule includes one inner capsule for mixing two materials.

7. The capsule assembly according to claim 1, wherein said outer capsule includes two or more inner capsules for mixing three or more materials.

8. A mixing capsule assembly for mixing a plurality of materials by vibration, comrpising: an outer capsule to receive one of the materials to be mixed; and an inner capsule to receive a second material to be mixed, and to be enclosed within said outer capsule; said outer capsule being constituted of two sections having frictionally-engaging surfaces for attaching them together to enclose said one material and the inner capsule; said inner capsule including two sections attachable together to enclose said second material and to prevent it from mixing with said first material; said two sections of the inner capsule being attachable together by at least one pair of complementary, frictionally-engaging surfaces configured such that when the inner capsule is impacted against one inner face of the outer capsule during the vibration of the capsule assembly, said complementary surfaces are moved away from each other to permit some of said second material to pass therebetween and to mix with said one material, and when the inner capsule is impacted against the opposite inner face of the outer capsule during the vibration of the capsule assembly, said complementary surfaces are moved back against each other to block the passage therebetween of said second material; said pair of complementary surfaces being constituted by the sides of a bore formed centrally in one of said sections, and the sides of a stem formed centrally in the other of said sections; the opposite ends of said two sections of the inner capsule being also in frictional engagement with each other.

9. The capsule assembly according to claim 8, wherein said bore in one section is of conical configuration, increasing in diameter from the outer to the inner end thereof, and the outer end of said stem in the other section is of complementary conical configuration and normally projects past the outer face of said one section so as to be impacted against the inner face of the outer capsule during the vibration of the capsule assembly.

10. The capsule assembly according to claim 8, wherein said bore in one section decreases in diameter from the outer end to the inner end thereof, and the outer end of said stem in the other section is of complementary conical configuration and normally is recessed within said bore so that said one section of the inner capsule is impacted against the inner face of the outer capsule during the vibration of the capsule assembly, causing said stem to move further within said bore and thereby to permit the passage of the second material therethrough.

11. The capsule assembly according to claim 10, wherein the opposite end of said one section projects past the respective outer face of the other section such as to be impacted by the inner face of the outer capsule during the vibration of the capsule assembly, and thereby to permit some of said second material therein also to pass between the complementary surfaces at said opposite ends of the two sections of the inner capsule.

12. The capsule assembly according to claim 8, wherein said outer capsule includes one inner capsule for mixing two materials.

13. The capsule assembly according to claim 8, wherein said outer capsule includes two or more inner capsules for mixing three or more materials.

* * * * *